US009096626B2

(12) United States Patent
Haddad et al.

(10) Patent No.: US 9,096,626 B2
(45) Date of Patent: Aug. 4, 2015

(54) MONOPHOSPHORUS LIGANDS AND THEIR USE IN CROSS-COUPLING REACTIONS

(75) Inventors: Nizar Haddad, Danbury, CT (US); Bo Qu, Brookfield, CT (US); Sonia Rodriguez, New Milford, CT (US); Chris Senanayake, Brookfield, CT (US); Wenjun Tang, Southbury, CT (US); Xudong Wei, Ridgefield, CT (US); Nathan K. Yee, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 303 days.

(21) Appl. No.: 13/635,671

(22) PCT Filed: Mar. 31, 2011

(86) PCT No.: PCT/US2011/030681
§ 371 (c)(1),
(2), (4) Date: Jan. 28, 2013

(87) PCT Pub. No.: WO2011/126917
PCT Pub. Date: Oct. 13, 2011

(65) Prior Publication Data
US 2013/0137902 A1 May 30, 2013

Related U.S. Application Data

(60) Provisional application No. 61/320,871, filed on Apr. 5, 2010.

(51) Int. Cl.
*C07F 9/6571* (2006.01)
*C07B 37/04* (2006.01)
*C07F 9/6568* (2006.01)

(52) U.S. Cl.
CPC ............ *C07F 9/657163* (2013.01); *C07B 37/04* (2013.01); *C07F 9/65683* (2013.01); *C07F 9/65685* (2013.01)

(58) Field of Classification Search
USPC .................................................. 568/8, 12, 14
See application file for complete search history.

(56) References Cited

U.S. PATENT DOCUMENTS 8,552,212 B2 * 10/2013 Qu et al. ..................... 556/18

FOREIGN PATENT DOCUMENTS

| JP | 2008247881 A | 10/2008 |
| WO | 2003042135 A2 | 5/2003 |
| WO | 2004052939 A2 | 6/2004 |
| WO | 2009076622 A2 | 6/2009 |

OTHER PUBLICATIONS

Tang et al: "Novel, Tunable, and Efficient Chiral Bisdihydrobenzooxaphosphole Ligands for Asymmetric Hydrogenation", Organic Letters, American Chemical Society, US, vol. 12, No. 1, Jan. 1, 2010, pp. 176-179.
Tang et al: "Novel and Efficient Chiral Bisphosphorus Ligands for Rhodium-Catalyzed Asymmetric Hydr. ogenat ton" Organic Letter;, American Chemical Society, US, vol. 12, No. 5, Jan. 1, 2010, pp. 1104-1107.
Rodriguez et al: "Oxaphosphole-Based Monophosphorus Ligands for Palladium-Catalyzed Amination Reactions" Advanced Sgnthesis I Catalysis, vol . 353, No. 4, Mar. 2, 2011, pp. 533-537.
Tang et al: "A General and Special Catalyst for Suzuki-Miyaura Coupling Processes", Angewandte Chemie International Edition, Jul. 15, 2010, pp. 5879-5883.
Tang et al: "Efficient Monophosphorus Ligands for Pal 1 adium-Catalyzed M i yaura Boryl at i o n", Organic Letters, vol. 13, No. 6, Feb. 14, 2011, pp. 1366-1369.
International Search Report, Form PCT/ISA/210, and Written Opinion, Form PCT/ISA/237, for cooresponding application PCT/US2011/030681, date of mailing Jul. 7, 2011.
Abstract in English for JP 2008247881, 2008.

* cited by examiner

*Primary Examiner* — Sudhakar Katakam
*Assistant Examiner* — Pancham Bakshi
(74) *Attorney, Agent, or Firm* — Michael P. Morris; Alan R. Stempel

(57) ABSTRACT

Phosphine ligands of the formula Ia, IB and mixtures thereof.

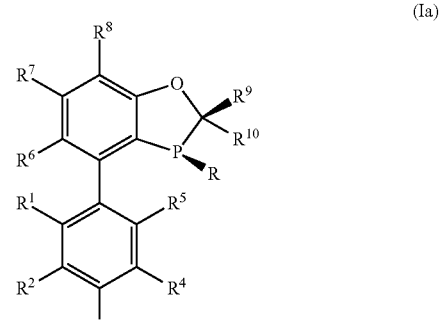

(Ia)

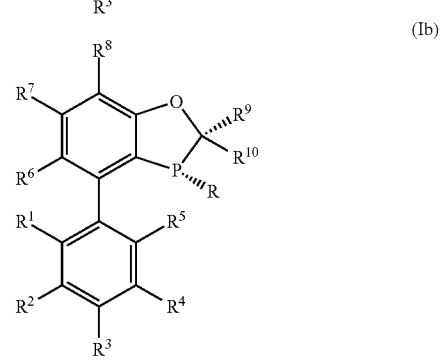

(Ib)

9 Claims, No Drawings

MONOPHOSPHORUS LIGANDS AND THEIR USE IN CROSS-COUPLING REACTIONS

BACKGROUND OF THE INVENTION

1. Technical Field

The present invention relates to a series of novel P-chiral monophosphorus ligands derived from a dihydrobenzo[1,3] oxaphosphole framework and their metal complexes as catalysts for applications in cross-coupling reaction. More particularly, the present invention relates to these phosphine ligands and their related catalysts for transition metal catalyzed cross-coupling reactions including carbon-carbon bond forming reactions and C—X cross-coupling reactions.

2. Background Information

Metal-catalyzed cross-coupling has become one of the most important transformations in organic chemistry. A. de Meijere, F. Diederich, Eds. *Metal-Catalyzed Cross-Coupling Reactions*, Vol. 2: Wiley-VCH, Weinheim, 2004. J.-P. Corbet, G. Mignani, *Chem. Rev.* 2006, 106, 2651. Development of efficient chiral or nonchiral ligands for metal-catalyzed cross-coupling has gained particular attention in the latest twenty years. As ligands have played essential roles during each step of the catalytic cycle including oxidative addition, transmetallation, and reductive elimination, the steric and electronic properties of ligand can greatly influence the rate, regioselectivity, and stereoselectivity of the cross-coupling reaction. Recent advances pioneered by Buchwald (T. E. Barder, S. D. Walker, J. R. Martinelli, S. L. Buchwald, *J. Am. Chem. Soc.* 2005, 127, 4685; S. D. Walker, T. E. Barder, J. R. Martinelli, S. L. Buchwald, *Angew. Chem., Int. Ed.* 2004, 43, 1871; K. Billingsley, S. L. Buchwald, *J. Am. Chem. Soc.* 2007, 129, 3358; S. L. Buchwald, B. P. Fors, D. S. Surry, WO2009/076622), Hartwig (J. F. Hartwig, Q. Shelby, N. Kataoka, WO 2002/011883; M. Driver, J. F. Hartwig, *J. Am. Chem. Soc.* 1996, 118, 7217), Fu (M. R. Netherton, C. Dai, K. Neuschuta, G. C. Fu, *J. Am. Chem. Soc.* 2001, 123, 10099; J. H. Kirchoff, M. R. Netherton, I. D. Hills, G. C. Fu, *J. Am. Chem. Soc.* 2002, 124, 13662), and Beller et al (A. Zapf, A, Ahrentraut, M. Beller *Angew. Chem., Int. Ed.* 2000, 39, 4153; A. Ahrentraut, A. Zapf, M. Beller, *Adv. Synth. Catal.* 2002, 344, 209; A. Zapf, R. Jackstell, F. Rataboul, T. Riermeier, A. Monsees, C. Fuhrmann, N. Shaikh, U. Dingerdissen, M. Beller, *Chem. Comm.* 2004, 38) have led to the development of many efficient ligands for cross-coupling reactions including carbon-carbon bond forming reactions and C—X cross-coupling reactions. Some efficient ligands are summarized below:

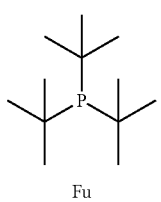

Fu

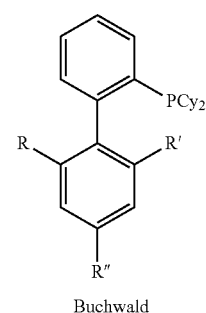

Buchwald

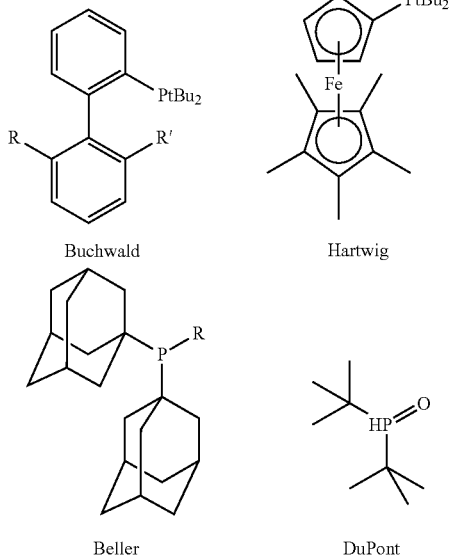

Buchwald    Hartwig

Beller    DuPont

The Suzuki-Miyaura coupling has become one of most useful method for formation of carbon-carbon bonds and has been used in numerous synthetic ventures. (N. Miyaura, *Topics in Current Chem.* 2002, 219, 11; A. Suzuki, *Organomet. Chem.* 1999, 576, 147). Despite the recent advances on this reaction, the Suzuki-Miyaura coupling of sterically hindered substrates and further decrease of the catalyst loading remain great challenges. Development of new ligands for Suzuki-Miyaura coupling reaction remains imperative to further increase its efficiency and expand its substrate scope.

BRIEF SUMMARY OF THE INVENTION

The invention provides a series of novel and efficient chiral monophosphorus ligands derived from a dihydrobenzo[1,3] oxaphosphole framework that has shown superior results for Suzuki coupling or asymmetric Suzuki reaction. High reactivity and selectivity have been observed in a sterically-congested asymmetric Suzuki coupling.

DETAILED DESCRIPTION OF THE INVENTION

In its first aspect, the present invention provides compounds of the formula (Ia), (Ib), or a mixture thereof:

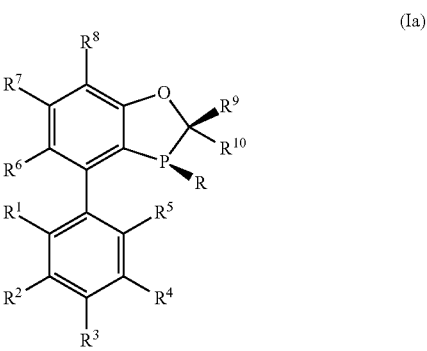

(Ia)

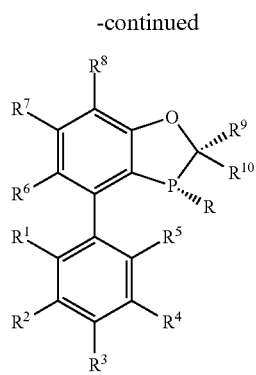

(Ib)

wherein:

R is (C$_1$-C$_6$)-alkyl, CF$_3$, (C$_3$-C$_{10}$)-carbocyclyl, (5- to 11-membered)heterocarbocyclyl, (C$_6$-C$_{10}$)aryl, (5 to 11-membered)heteroaryl, or ferrocenyl, wherein each such (C$_3$-C$_{10}$)carbocyclyl, (5- to 11-membered)heterocarbocyclyl, (C$_6$-C$_{10}$)aryl or (5 to 11-membered)heteroaryl group is optionally substituted with 1 to 3 substituents independently selected from the group consisting of —O(C$_1$-C$_6$)alkyl, (C$_1$-C$_6$)alkyl, and CF$_3$;

R$^1$, R$^2$, R$^3$, R$^4$, R$^5$ are each independently selected from the group consisting of H, halo, CF$_3$, —O(C$_1$-C$_6$)alkyl, (C$_1$-C$_6$)alkyl, (C$_3$-C$_{10}$)carbocyclyl, (5- to 11-membered)heterocarbocyclyl, (C$_6$-C$_{10}$)aryl, (5 to 11-membered)heteroaryl, —NR$^{11}$R$^{12}$, —Si(R$^{11}$)$_3$ and —SR$^{11}$, wherein each such (C$_3$-C$_{10}$)carbocyclyl, (5- to 11-membered)heterocarbocyclyl, (C$_6$-C$_{10}$)aryl or (5 to 11-membered)heteroaryl group is optionally substituted with 1 to 3 substituents independently selected from the group consisting of —O(C$_1$-C$_6$)alkyl, (C$_1$-C$_6$)alkyl and CF$_3$; or any two adjacent instances of R$^1$, R$^2$, R$^3$, R$^4$, R$^5$, taken together with the carbons to which they are bound, form a five- or six-membered substituted or unsubstituted aryl or heteroaryl ring; provided that at least one of R$^1$, R$^2$, R$^3$, R$^4$, R$^5$ are OR$^{11}$;

R$^6$, R$^7$, R$^8$ are each independently selected from the group consisting of H, CF$_3$, —O(C$_1$-C$_6$)alkyl, (C$_1$-C$_6$)alkyl, (C$_3$-C$_{10}$)carbocyclyl, (5- to 11-membered)heterocarbocyclyl, (C$_3$-C$_{10}$)aryl, (5 to 11-membered)heteroaryl and —NR$^{11}$R$^{12}$; wherein each such (C$_3$-C$_{10}$)carbocyclyl, (5- to 11-membered)heterocarbocyclyl, (C$_6$-C$_{10}$)aryl or (5 to 11-membered)heteroaryl group is optionally substituted with 1 to 3 substituents independently selected from the group consisting of —O(C$_1$-C$_6$)alkyl, (C$_1$-C$_6$)alkyl, and CF$_3$;

R$^9$, R$^{10}$ are each independently selected from the group consisting of H, (C$_1$-C$_6$)alkyl, (C$_3$-C$_6$)cycloalkyl, (3- to 6-membered)heterocycloalkyl, (C$_6$-C$_{10}$)aryl, (5- to 6-membered)heteroaryl, and —SiR$^5$$_3$; wherein each such (C$_3$-C$_6$)cycloalkyl, (3- to 6-membered)heterocycloalkyl, (C$_6$-C$_{10}$)aryl or (5- to 6-membered)heteroaryl group is optionally substituted with 1 to 3 substituents independently selected from the group consisting of —O(C$_1$-C$_6$)alkyl, (C$_1$-C$_6$)alkyl, and CF$_3$;

R$^{11}$ and R$^{12}$ are each independently selected from the group consisting of H, (C$_1$-C$_6$)alkyl, CF$_3$, (C$_3$-C$_{10}$)carbocyclyl, (5- to 11-membered)heterocarbocyclyl, (C$_6$-C$_{10}$)aryl, and (5 to 11-membered)heteroaryl, wherein each such (C$_3$-C$_{10}$)carbocyclyl, (5- to 11-membered)heterocarbocyclyl, (C$_6$-C$_{10}$)aryl or (5 to 11-membered)heteroaryl group is optionally independently substituted with 1 to 3 substituents independently selected from the group consisting of halo, —O(C$_1$-C$_6$)alkyl, (C$_1$-C$_6$)alkyl, and —CF$_3$.

In a second aspect, the invention relates to compounds of formula (Ia), (Ib), or a mixture thereof, wherein R is —(C$_1$-C$_6$)alkyl selected from —CH$_3$, —CH$_2$CH$_3$, —CH(CH$_3$)$_2$, —C(CH$_3$)$_3$, —C(CH$_2$CH$_3$)$_3$, and —C(CH$_2$CH$_3$)(CH$_3$)$_2$, and R$^1$, R$^2$, R$^3$, R$^4$, R$^5$, R$^6$, R$^7$, R$^8$, R$^9$, R$^{10}$, R$^{11}$ and R$^{12}$ are as defined in the first aspect.

In a third aspect, the invention provides compounds of the formula (Ia), (Ib), or a mixture thereof, wherein R is —(C$_3$-C$_{10}$)carbocyclyl selected from cyclopentyl, cyclohexyl, and 1-adamantyl, and R$^1$, R$^2$, R$^3$, R$^4$, R$^5$, R$^6$, R$^7$, R$^8$, R$^9$, R$^{10}$, R$^{11}$ and R$^{12}$ are as defined in the first aspect.

In a fourth aspect, the invention provides compounds of the formula (Ia), (Ib), or a mixture thereof, wherein R is —(C$_6$-C$_{10}$)aryl selected from phenyl, ortho-tolyl, para-tolyl, 3,5-dimethylphenyl, 3,5-di-t-butylphenyl, 3,5-di-CF$_3$-phenyl, ortho-CF$_3$-phenyl, ortho-anisyl, and naphthyl, and R$^1$, R$^2$, R$^3$, R$^4$, R$^5$, R$^6$, R$^7$, R$^8$, R$^9$, R$^{10}$, R$^{11}$ and R$^{12}$ are as defined in the first aspect.

In a fifth aspect, the invention provides compounds of the formula (Ia), (Ib), or a mixture thereof, wherein R$^1$, R$^2$, R$^3$, R$^4$, R$^5$ are each independently H, —CH$_3$, —CH$_2$CH$_3$, —CH(CH$_3$)$_2$, —C(CH$_3$)$_3$, —OCH$_3$, —OCH$_2$CH$_3$, —OCH(CH$_3$)$_2$, N(CH$_3$)$_2$, N(CH$_2$CH$_3$)$_2$, or SiMe$_3$, and R, R$^6$, R$^7$, R$^8$, R$^9$, R$^{10}$, R$^{11}$ and R$^{12}$ are as defined in the first, second, third or fourth aspect.

In a sixth aspect, the invention provides compounds of the formula (Ia), (Ib), or a mixture thereof, wherein R$^6$, R$^7$, R$^8$ are H, and R, R$^1$, R$^2$, R$^3$, R$^4$, R$^5$, R$^9$, R$^{10}$, R$^{11}$ and R$^{12}$ are as defined in the first, second, third, fourth or fifth aspect.

In a seventh aspect, the invention provides compounds of the formula (Ia), (Ib), or a mixture thereof, R$^9$ and R$^{10}$ are each independently H, —CH$_3$, —CH$_2$CH$_3$, —CH(CH$_3$)$_2$, —C(CH$_3$)$_3$, phenyl, ortho-tolyl, para-tolyl, 3,5-dimethylphenyl, 3,5-di-t-butylphenyl, 3,5-di-CF$_3$-phenyl, ortho-CF$_3$-phenyl, ortho-anisyl, 2,6-dimethoxyphenyl or naphthyl, and R, R$^1$, R$^2$, R$^3$, R$^4$, R$^5$, R$^6$, R$^7$, R$^8$, R$^{11}$ and R$^{12}$ are as defined in the first, second, third, fourth, fifth aspect or sixth aspect.

In an eighth aspect, the invention provides a phosphine ligand having the formula (IIa) or (IIb), or a mixture thereof,

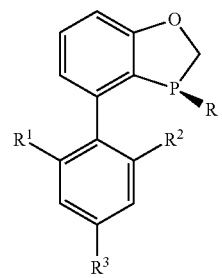

(IIa)

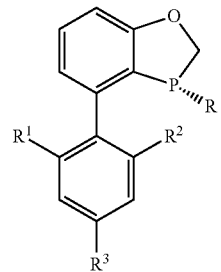

(IIb)

wherein:

R is —CH(CH$_3$)$_2$, —C(CH$_3$)$_3$—C(CH$_2$CH$_3$)(CH$_3$)$_2$, cyclohexyl, 1-adamantyl, phenyl, ortho-tolyl, 3,5-xylyl, ortho-anisyl, or ferrocenyl; and R$^1$, R$^2$, and R$^3$ are independently H, —CH$_3$, —CH$_2$CH$_3$, —CH(CH$_3$)$_2$, —C(CH$_3$)$_3$, —OCH$_3$, —OCH$_2$CH$_3$, —OCH(CH$_3$)$_2$, OPh, N(CH$_3$)$_2$, N(CH$_2$CH$_3$)$_2$, SiMe$_3$, CF$_3$.

More particularly, the invention provides phosphine ligands selected from the group consisting of:

(S) and (R)-3-tert-butyl-4-phenyl-2,3-dihydrobenzo[d][1,3]oxaphosphole, (S) and (R)-3-tert-butyl-4-(2,6-dimethoxyphenyl)-2,3-dihydrobenzo[d][1,3]oxaphosphole, (S) and (R)-2-(3-tert-butyl-2,3-dihydrobenzo[d][1,3]oxaphosphol-4-yl)-N1,N1,N3,N3-tetramethylbenzene-1,3-diamine, (S) and (R)-2-(3-tert-butyl-2,3-dihydrobenzo[d][1,3]oxaphosphol-4-yl)-N,N-dimethylaniline, (S) and (R)-3-tert-butyl-4-(2-methoxyphenyl)-2,3-dihydrobenzo[d][1,3]oxaphosphole, (S) and (R)-3-tert-butyl-4-(2,6-diisopropoxyphenyl)-2,3-dihydrobenzo[d][1,3]oxaphosphole, (S) and (R)-3-tert-butyl-4-(2,4,6-triisopropylphenyl)-2,3-dihydrobenzo[d][1,3]oxaphosphole, (S) and (R)-3-tert-butyl-4-o-tolyl-2,3-dihydrobenzo[d][1,3]oxaphosphole, (S) and (R)-3-tert-butyl-4-(2-phenoxyphenyl)-2,3-dihydrobenzo[d][1,3]oxaphosphole, (S) and (R)-3-cyclohexyl-4-phenyl-2,3-dihydrobenzo[d][1,3]oxaphosphole, (S) and (R)-3-cyclohexyl-4-(2,6-dimethoxyphenyl)-2,3-dihydrobenzo[d][1,3]oxaphosphole, (S) and (R)-2-(3-cyclohexyl-2,3-dihydrobenzo[d][1,3]oxaphosphol-4-yl)-N1,N1,N3,N3-tetramethylbenzene-1,3-diamine, (S) and (R)-2-(3-cyclohexyl-2,3-dihydrobenzo[d][1,3]oxaphosphol-4-yl)-N,N-dimethylaniline, (S) and (R)-3-cyclohexyl-4-(2-methoxyphenyl)-2,3-dihydrobenzo[d][1,3]oxaphosphole, (S) and (R)-3-cyclohexyl-4-(2,4,6-triisopropylphenyl)-2,3-dihydrobenzo[d][1,3]oxaphosphole, (S) and (R)-3-cyclohexyl-4-(2,6-diisopropoxyphenyl)-2,3-dihydrobenzo[d][1,3]oxaphosphole, (S) and (R)-3-cyclohexyl-4-o-tolyl-2,3-dihydrobenzo[d][1,3]oxaphosphole, and (S) and (R)-3-cyclohexyl-4-(2-phenoxyphenyl)-2,3-dihydrobenzo[d][1,3]oxaphosphole.

The present invention further provides a catalyst prepared by a process including contacting a transition metal salt, or a complex thereof, and a chiral ligand according to the present invention as described.

The present invention further provides a process for preparation of a chiral or nonchiral compound by employing a ligand or catalyst according to the present invention as described herein above.

In another aspect, the present invention provides a process for preparation of the above-described ligands of formulas Ia, Ib, II and IIb. In general, these ligands may be prepared in the manner depicted in the general reaction scheme below.

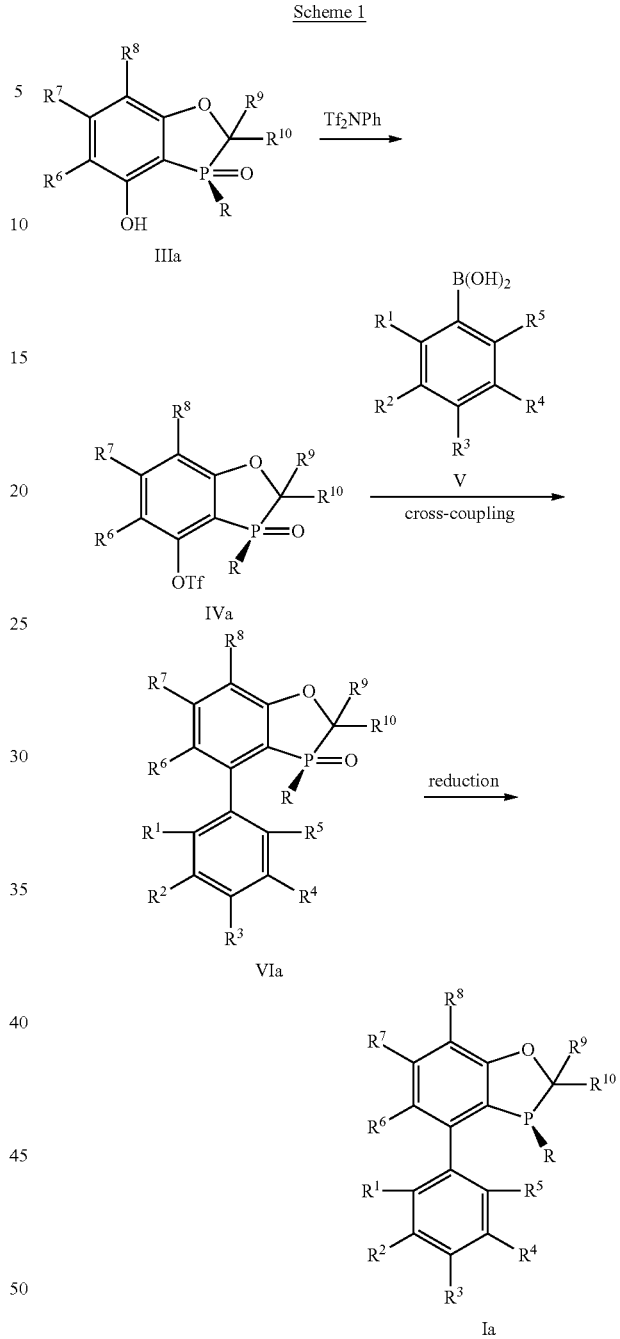

Scheme 1

As illustrated in Scheme 1, phenol IIIa, or its enantiomer, or a mixture of thereof is converted into a triflate IVa, or its enantiomer, or a mixture of thereof, by reacting with Tf$_2$NPh or trifluoromethylsulfonyl anhydride in a suitable solvent such as dichloromethane, THF, or toluene. Cross-coupling of triflate IVa with a boronic acid of formula V with a catalytic amount of a palladium precursor such as Pd(OAc)$_2$ or Pd$_2$dba$_3$ and a suitable phosphorus ligand such as S-Phos, Cy$_3$P, or a ligand of formula Ia described in this invention, provides the biaryl product of formula VIa. Reduction of this phosphine oxide VIa under a reaction condition of polymethylhydrosiloxane (PMHS)/Ti(OiPr)$_4$, PhSiH$_3$, HSiCl$_3$/Et$_3$N, or DIBAL, provides the ligand of formula Ia, or its enantiomer, or a mixture of thereof.

Starting compounds of the formula Ma may be made in the manner described by Tang et al., Organic Letters, Vol. 12, No. 1, pp 176-179 (2010) and Tang et al., Organic Letters, Vol. 12, No. 5, pp 1104-1107 (2010).

The process for making the ligands of the invention may be better understood by having reference to the following examples.

Example 1

(S)-3-tert-butyl-2,3-dihydrobenzo[d][1,3]oxaphosphol-4-yl trifluoromethanesulfonate oxide

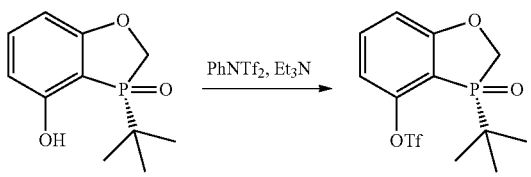 [SMILES: CC(C)(C)[P@@]1(=O)COc2cccc(O)c21 ; CC(C)(C)[P@@]1(=O)COc2cccc(OS(=O)(=O)C(F)(F)F)c21]

To a solution of (S)-3-tert-butyl-2,3-dihydrobenzo[d][1,3]oxaphosphol oxide-4-ol (50 mg, 0.221 mmol) and triethylamine (89 mg, 0.88 mmol, 4 equiv) in $CH_2Cl_2$ (2 mL) at 0° C. was added $Tf_2NPh$ (96 mg, 0.27 mmol, 1.2 equiv) over 1 min. The mixture was stirred at rt for 2 h and then quenched with addition of water (2 mL). The $CH_2Cl_2$ layer was separated, dried over sodium sulfate, concentrated, and purified by silica gel column chromatography (eluents: hexanes to EtOAc) to provide (S)-3-tert-butyl-2,3-dihydrobenzo[d][1,3]oxaphosphol-4-yl trifluoromethanesulfonate oxide (75 mg, 0.21 mmol, 95%) as white solid. $^1$HNMR (500 MHz, $CD_2Cl_2$) δ 7.58 (t, J=8.3 Hz, 1H), 7.03 (dd, J=8.2, 3.5 Hz, 1H), 7.00 (dd, J=8.5, 2.4 Hz, 1H), 4.67 (dd, J=14.2, 2.1 Hz, 1H), 4.46 (dd, J=14.1, 11.1 Hz, 1H), 1.21 (d, J=16.8 Hz, 9H); $^{31}$PNMR (202 MHz, $CD_2Cl_2$) δ 75.6; $^{13}$CNMR (125 MHz, $CD_2Cl_2$) δ167.1 (d, J=16.8 Hz), 150.0, 137.1, 120.3, 117.8, 114.7 (d, J=4.4 Hz), 114.2 (d, J=4.3 Hz), 66.9 (d, J=59.3 Hz), 34.7 (d, J=72.0 Hz), 24.2; ESI-MS: m/z 359 [M+H]$^+$.

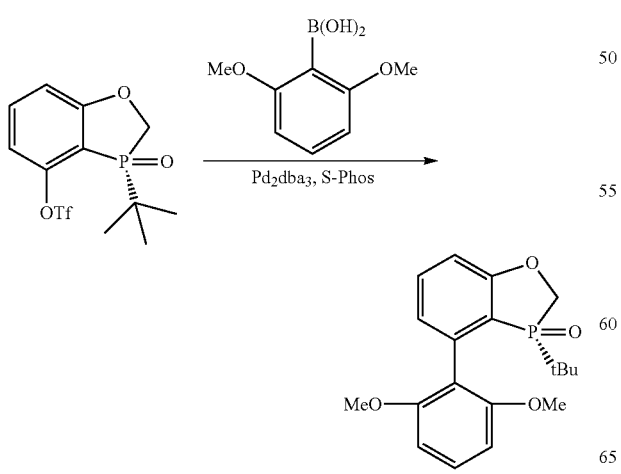

Example 2

(S)-3-tert-butyl-4-(2,6-dimethoxyphenyl)-2,3-dihydrobenzo[d][1,3]oxaphosphole oxide by Suzuki Coupling with S-phos as the Ligand To a solution of (S)-3-tert-butyl-2,3-dihydrobenzo[d][1,3]oxaphosphol-4-yl trifluoromethanesulfonate oxide (5 g, 13.9 mmol) and 2,6-dimethoxyphenylboronic acid (3.8 g, 20.9 mmol, 1.5 equiv), $Pd_2dba_3$ (383 mg, 0.42 mmol, 3 mol %), S-Phos (1.15 g, 2.79 mmol, 20 mol %) and KF (3.24 g, 55.8 mmol, 4 equiv) was charged degassed dioxane (30 mL). The mixture was stirred under nitrogen at 100° C. for 12 h. The mixture was cooled to rt and concentrated. To the residue was added DCM (30 mL) and 2 N NaOH (30 mL). The DCM layer was further washed with 2 N NaOH (30 mL) and brine (30 mL), dried over sodium sulfate, and concentrated. The residue was purified by column chromatography (hexane to EtOAc/MeOH 2/1) to provide the desired product as yellow solid (3 g, 8.66 mmol, 62%). $^1$HNMR (500 MHz, $CDCl_3$): δ=7.46 (t, J=7.9 Hz, 1H), 7.28 (t, J=8.4 Hz, 1H), 6.89 (m, 2H), 6.64 (d, J=8.4 Hz, 1H), 6.55 (d, J=8.4 Hz, 1H), 4.47 (dd, J=13.8, 1.8 Hz, 1H), 4.34 (dd, J=13.7, 10.5 Hz, 1H), 3.77 (s, 3H), 3.70 (s, 3H), 0.87 (d, J=15.9 Hz, 9H); $^{31}$PNMR (202 MHz, $CDCl_3$): δ=62.4; $^{13}$CNMR (125 MHz, $CDCl_3$): δ=165.2 (d, J=18.8 Hz), 158.5, 157.3, 138.1 (d, J=6.3 Hz), 134.0 (d, J=1.3 Hz), 129.8, 125.0 (d, J=8.8 Hz), 117.4 (d, J=2.5 Hz), 114.8, 114.0, 112.4 (d, J=5.0 Hz), 104.3, 103.1, 65.3 (d, J=60.0 Hz), 55.8, 55.3, 33.4 (d, J=71.3 Hz), 23.6 (d, J=1.3 Hz); ESI-MS: m/z 347 [M+H]$^+$.

Example 3

(S)-3-tert-butyl-4-(2,6-dimethoxyphenyl)-2,3-dihydrobenzo[d][1,3]oxaphosphole oxide by Suzuki coupling with (R)-3-tert-butyl-4-(2,6-dimethoxyphenyl)-2,3-dihydrobenzo[d][1,3]oxaphosphole as the ligand

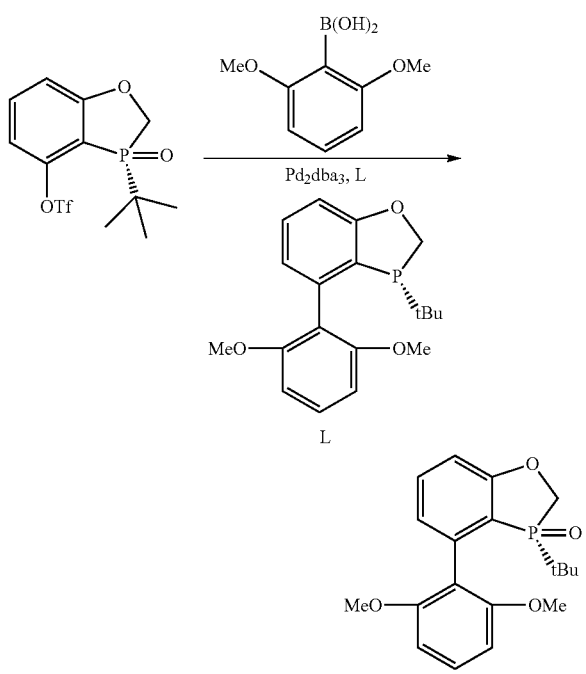

To a mixture of (S)-3-tert-butyl-2,3-dihydrobenzo[d][1,3] oxaphosphol-4-yl rifluoromethanesulfonate oxide (215 g, 600 mmol) and 2,6-dimethoxyphenylboronic acid (164 g, 900 mmol, 1.5 equiv), Pd$_2$dba$_3$ (6.9 g, 7.5 mmol, 0.0125 equiv), (R)-3-tert-butyl-4-(2,6-dimethoxyphenyl)-2,3-dihydrobenzo[d][1,3]oxaphosphole (5.9 g, 18 mmol, 0.03 equiv) and KF (139 g, 2.4 mol, 4 equiv) was charged degassed dioxane (2 L). The mixture was stirred under nitrogen at 100° C. for 3 h, then cooled to rt and concentrated to remove most dioxane. To the residue was added DCM (1000 mL) and 2 N NaOH (500 mL). The DCM layer was further washed with 2 N NaOH (500 mL) and brine (500 mL), dried over sodium sulfate, and concentrated. The residue was purified by column chromatography (eluent: hexane to EtOAc/MeOH 2/1) to provide the desired product (S)-3-tert-butyl-4-(2,6-dimethoxyphenyl)-2,3-dihydrobenzo[d][1,3]oxaphosphole oxide (190 g, 576 mmol, 91%) as white solid.

Example 4

(R)-3-tert-butyl-4-(2,6-dimethoxyphenyl)-2,3-dihydrobenzo[d][1,3]oxaphosphole

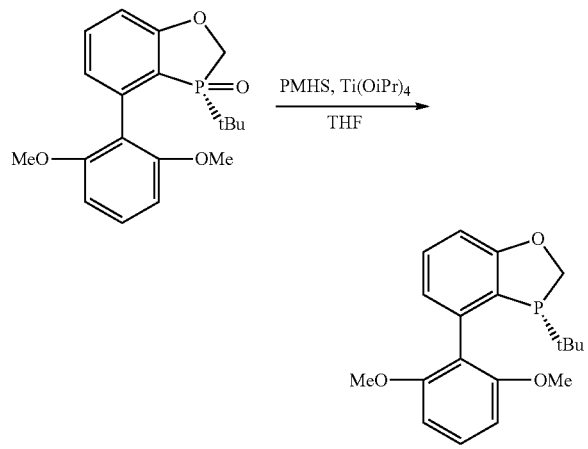

To a solution of (S)-3-tert-butyl-4-(2,6-dimethoxyphenyl)-2,3-dihydrobenzo[d][1,3]oxaphosphole oxide (6.5 g, 18.8 mmol) in THF (65 mL) at rt was added PMHS (13 g) and Ti(OiPr)$_4$ (6.4 g, 22.5 mmol, 1.2 equiv). The mixture was stirred at reflux for 12 h, then concentrated under vacuum to remove most THF. To the residue treated carefully with 30% NaOH solution (60 mL). Gas was generated during addition. The resulting mixture was further stirred at 60° C. for 0.5 h. To the mixture at rt was added MTBE (60 mL). The MTBE layer was separated and the aqueous layer was washed with MTBE under nitrogen. The MTBE solution was dried, concentrated, and purified by passing through a neutral alumina plug to give the desired product as white crystalline solid (5 g, 15.1 mmol, 81%). $^1$HNMR (400 MHz, CDCl$_3$): δ=7.29 (m, 2H), 6.87 (m, 2H), 6.65 (d, J=8.2 Hz, 1H), 6.59 (d, J=8.3 Hz, 1H), 4.81 (dd, J=12.5, 1.8 Hz, 1H), 4.53 (dd, J=25.2, 12.5 Hz, 1H), 3.77 (s, 3H), 3.71 (s, 3H), 0.73 (d, J=12.1 Hz, 9H); $^{31}$PNMR (162 MHz, CDCl$_3$): δ=−7.9; $^{13}$CNMR (100 MHz, CDCl$_3$): δ=163.4, 157.9, 157.1, 138.4 (d, J=22.3 Hz), 130.5, 129.0, 125.0 (d, J=16.4 Hz), 123.8 (d, J=5.4 Hz), 119.6, 109.5, 104.5, 103.6, 70.4 (d, J=33.8 Hz), 55.9, 55.4, 30.9 (d, J=23.2 Hz), 26.6 (d, J=18.1 Hz); ESI-MS: m/z 331 [M+H]$^+$.

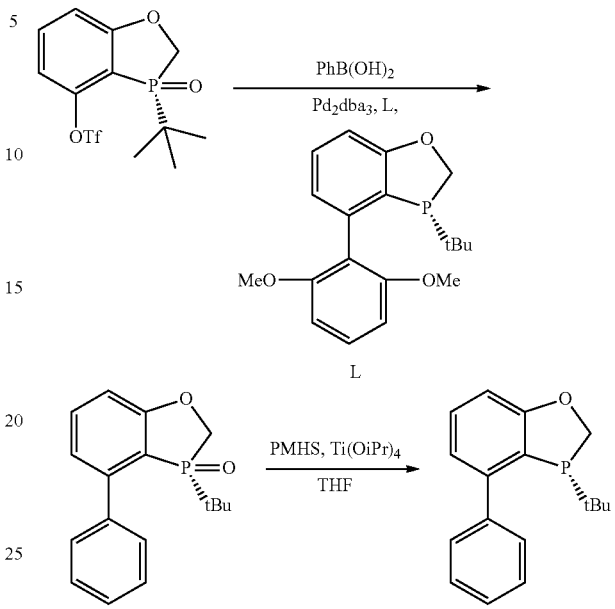

Example 5

(S)-3-tert-butyl-4-phenyl-2,3-dihydrobenzo[d][1,3] oxaphosphole oxide (S)-3-tert-butyl-4-phenyl-2,3-dihydrobenzo[d][1,3]oxaphosphole oxide was prepared under a similar condition described in Example 3: 90% yield; $^1$HNMR (400 MHz, CDCl$_3$): δ=7.76 (d, J=7.4 Hz, 1H), 7.41-7.53 (m, 3H), 7.36 (m, 1H), 7.05 (dd, J=7.5, 3.6 Hz, 1H), 6.91 (dd, J=8.3, 3.2 Hz, 1H), 4.56 (dd, J=13.7, 1.1 Hz, 1H), 4.44 (dd, J=13.8, 10.5 Hz, 1H), 0.78 (d, J=16.1 Hz, 9H); $^{31}$PNMR (162 MHz, CDCl$_3$): δ=65.1; $^{13}$CNMR (100 MHz, CDCl$_3$): δ=165.7 (d, J=19.2 Hz, 1H), 146.7 (d, J=5.8 Hz, 1H), 134.8 (d, J=1.7 Hz, 1H), 129.6, 128.5, 128.3, 123.4 (d, J=8.0 Hz), 112.5 (d, J=5.3 Hz), 112.4 (d, J=87.9 Hz), 65.2 (d, J=61.7 Hz), 33.8 (d, J=70.7 Hz), 23.7. ESI-MS: m/z 287 [M+H]$^+$.

Example 6

(R)-3-tert-butyl-4-phenyl-2,3-dihydrobenzo[d][1,3] oxaphosphole (R)-3-tert-butyl-4-phenyl-2,3-dihydrobenzo[d][1,3]oxaphosphole was prepared under a similar condition described in Example 4. 89%; $^1$HNMR (400 MHz, CD$_2$Cl$_2$): δ=7.71 (m, 2H), 7.42 (m, 2H), 7.35 (m, 2H), 6.99 (m, 1H), 6.90 (dd, J=8.1, 0.8 Hz, 1H), 4.87 (dd, J=12.7, 1.9 Hz, 1H), 4.57 (dd, J=25.9, 12.7 Hz, 1H), 0.64 (d, J=12.1 Hz, 9H); $^{31}$PNMR (162 MHz, CD$_2$Cl$_2$): δ=−11.2; $^{13}$CNMR (100 MHz, CD$_2$Cl$_2$): δ=164.8, 146.5, 143.1, 131.9, 129.9, 129.8, 128.9, 127.9, 122.7 (d, J=17.9 Hz), 122.3 (d, J=3.1 Hz), 110.5, 70.5 (d, J=26.9 Hz), 32.1 (d, J=20.2 Hz), 27.0 (d, J=13.8 Hz).

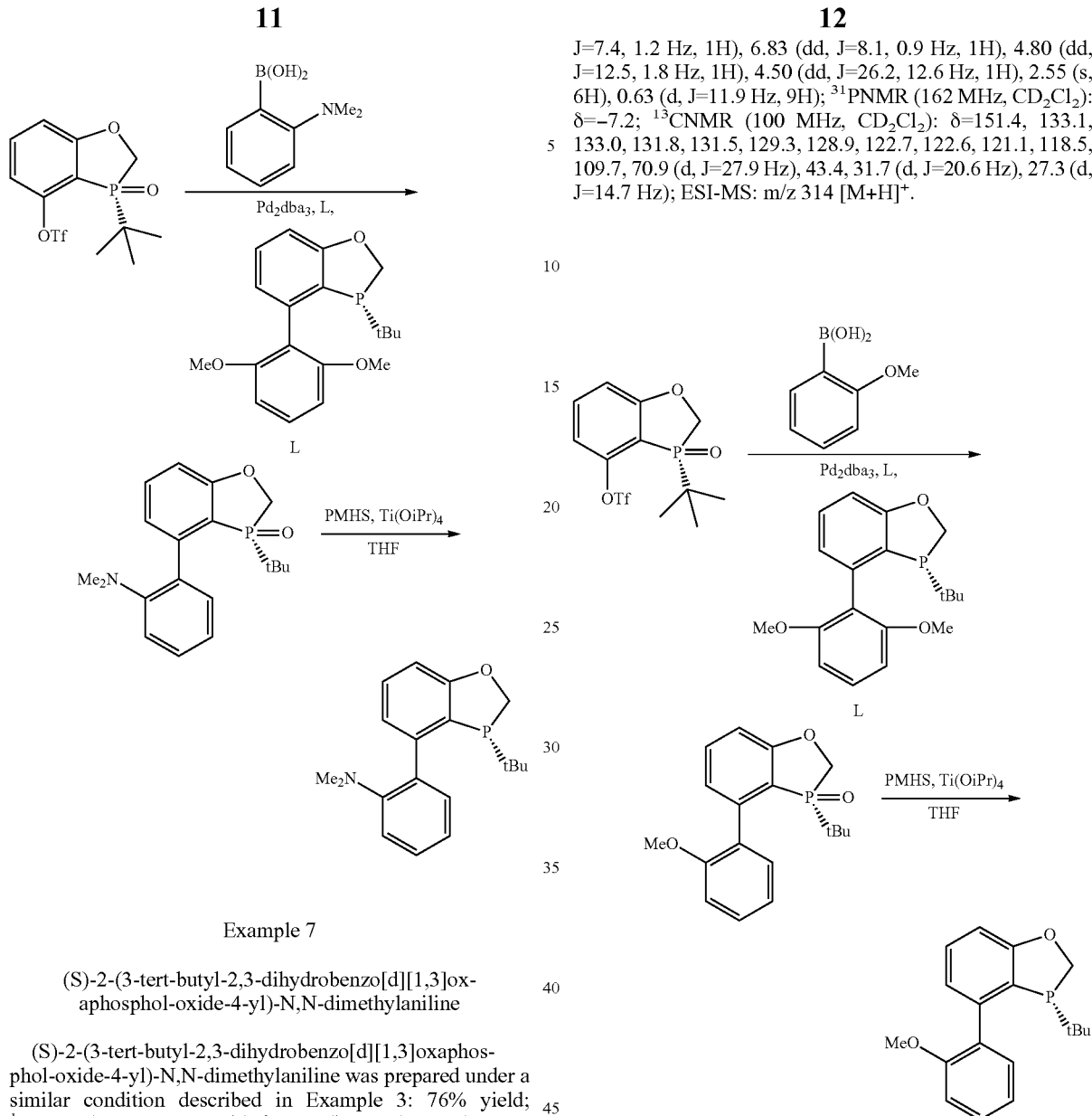

J=7.4, 1.2 Hz, 1H), 6.83 (dd, J=8.1, 0.9 Hz, 1H), 4.80 (dd, J=12.5, 1.8 Hz, 1H), 4.50 (dd, J=26.2, 12.6 Hz, 1H), 2.55 (s, 6H), 0.63 (d, J=11.9 Hz, 9H); $^{31}$PNMR (162 MHz, CD$_2$Cl$_2$): δ=−7.2; $^{13}$CNMR (100 MHz, CD$_2$Cl$_2$): δ=151.4, 133.1, 133.0, 131.8, 131.5, 129.3, 128.9, 122.7, 122.6, 121.1, 118.5, 109.7, 70.9 (d, J=27.9 Hz), 43.4, 31.7 (d, J=20.6 Hz), 27.3 (d, J=14.7 Hz); ESI-MS: m/z 314 [M+H]$^+$.

Example 7

(S)-2-(3-tert-butyl-2,3-dihydrobenzo[d][1,3]ox-aphosphol-oxide-4-yl)-N,N-dimethylaniline (S)-2-(3-tert-butyl-2,3-dihydrobenzo[d][1,3]oxaphos-phol-oxide-4-yl)-N,N-dimethylaniline was prepared under a similar condition described in Example 3: 76% yield; $^1$HNMR (400 MHz, CDCl$_3$): δ=7.74 (br s, 1H), 7.44 (t, J=7.6 Hz, 1H), 7.37 (br s, 1H), 7.29 (dd, J=8.0, 1.8 Hz), 7.03 (m, 1H), 7.01 (d, J=8.1 Hz, 1H), 6.87 (dd, J=9.1, 3.2 Hz, 1H), 4.54 (dd, J=13.9, 2.0 Hz, 1H), 4.41 (dd, J=13.8, 10.7 Hz, 1H), 2.59 (s, 6H), 0.88 (d, J=16.1 Hz, 9H); $^{31}$PNMR (162 MHz, CDCl$_3$): δ=64.1; $^{13}$CNMR (100 MHz, CDCl$_3$): δ=145.6 (d, J=5.5 Hz), 134.3, 133.4, 129.3, 124.1 (d, J=8.1 Hz), 121.2, 118.0, 112.1 (d, J=5.2 Hz), 65.5 (d, J=61.7 Hz), 43.4, 33.9 (d, J=71.3 Hz), 24.1; ESI-MS: m/z 330 [M+H]$^+$.

Example 8

(R)-2-(3-tert-butyl-2,3-dihydrobenzo[d][1,3]ox-aphosphol-4-yl)-N,N-dimethylaniline (R)-2-(3-tert-butyl-2,3-dihydrobenzo[d][1,3]oxaphos-phol-4-yl)-N,N-dimethylaniline was prepared under a similar condition described in Example 4: 63% yield; $^1$HNMR (400 MHz, CD$_2$Cl$_2$): δ=7.32 (t, J=7.7 Hz, 1H), 7.32 (br s, 1H), 7.24 (m, 1H), 7.04 (br s, 1H), 6.99 (dd, J=8.2, 1.0 Hz, 1H), 6.93 (dt,

Example 9

(S)-3-tert-butyl-4-(2-methoxyphenyl)-2,3-dihydrobenzo[d][1,3]oxaphosphole oxide ((S)-3-tert-butyl-4-(2-methoxyphenyl)-2,3-dihydrobenzo[d][1,3]oxaphosphole oxide was prepared under a similar condition described in Example 3: 85%; $^1$HNMR (500 MHz, CDCl$_3$): δ=7.61 (d, J=7.3 Hz, 1H), 7.44 (t, J=8.0 Hz, 1H), 7.34 (t, J=7.6 Hz, 1H), 7.05 (m, 2H), 6.95 (d, J=8.2 Hz, 1H), 6.90 (dd, J=8.3, 3.2 Hz, 1H), 4.51 (dd, J=13.8, 1.6 Hz, 1H), 4.41 (dd, J=13.8, 10.5 Hz, 1H), 3.79 (s, 3H), 0.82 (d, J=16.1 Hz, 9H); $^{31}$PNMR (202 MHz, CDCl$_3$): δ=63.6; $^{13}$CNMR (125 MHz, CDCl$_3$): δ=165.5 (d, J=19.1 Hz), 156.4, 142.3 (d, J=5.7 Hz), 133.7 (d, J=1.6 Hz), 132.7, 129.7, 128.8 (d, J=2.3 Hz), 125.0 (d, J=8.2 Hz), 120.5, 113.6 (d, J=89.4 Hz), 112.2 (d, J=5.4 Hz), 110.7, 65.4 (d, J=61.1 Hz), 55.4, 33.6 (d, J=71.1 Hz), 23.9 (d, J=1.1 Hz); ESI-MS: m/z 317 [M+H]$^+$.

Example 10

(R)-3-tert-butyl-4-(2-methoxyphenyl)-2,3-dihydrobenzo[d][1,3]oxaphosphole (R)-3-tert-butyl-4-(2-methoxyphenyl)-2,3-dihydrobenzo[d][1,3]oxaphosphole was prepared under a similar condition described in Example 4: 78%; $^1$HNMR (500 MHz, CD$_2$Cl$_2$): δ=7.41 (d, J=7.4 Hz, 1H), 7.33 (m, 1H), 7.29 (t, J=7.9 Hz, 1H), 7.00 (m, 2H), 6.94 (dd, J=7.4, 3.2 Hz, 1H), 6.87 (d, J=8.4 Hz, 1H), 4.83 (dd, J=12.6, 1.9 Hz, 1H), 4.54 (dd, J=25.7, 12.6 Hz, 1H), 3.78 (s, 3H), 0.67 (d, J=12.1 Hz, 9H); $^{31}$PNMR (202 MHz, CD$_2$Cl$_2$): δ=−9.9; $^{13}$CNMR (125 MHz, CD$_2$Cl$_2$): δ=164.4, 157.1, 143.3 (d, J=16.0 Hz), 132.5 (d, J=3.7 Hz), 131.8, 131.0, 129.5, 123.7 (d, J=3.6 Hz), 120.8, 111.7, 110.0 (d, J=1.0 Hz), 70.7 (d, J=23.3 Hz), 55.8 (d, J=0.8 Hz), 31.6 (d, J=19.7 Hz); 27.7 (d, J=14.3 Hz); ESI-MS: m/z 301 [M+H]$^+$.

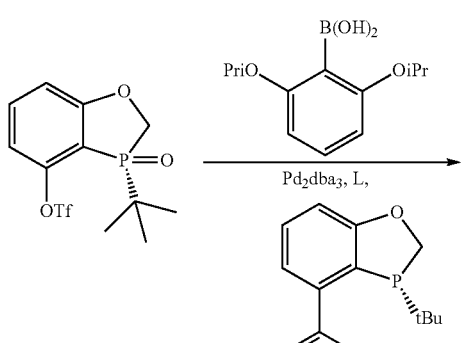

Example 11

(S)-3-tert-butyl-4-(2,6-diisopropoxy phenyl)-2,3-dihydrobenzo[d][1,3]oxaphosphole oxide (S)-3-tert-butyl-4-(2,6-diisopropoxyphenyl)-2,3-dihydrobenzo[d][1,3]oxaphosphole oxide was prepared under a similar condition described in Example 3: 27% yield; $^1$HNMR (500 MHz, CDCl$_3$): δ=7.43 (t, J=7.8 Hz, 1H), 7.20 (t, J=8.4 Hz, 1H), 6.84 (m, 2H), 6.56 (d, J=8.4 Hz, 1H), 6.47 (d, J=8.4 Hz, 1H), 4.47 (m, 3H), 4.31 (dd, J=13.6, 10.5 Hz, 1H), 1.31 (d, J=6.1 Hz, 3H), 1.22 (d, J=6.0 Hz, 3H), 1.17 (d, J=6.1 Hz, 6H), 0.92 (d, J=15.9 Hz, 9H); $^{31}$PNMR (202 MHz, CDCl$_3$): δ=61.7; ESI-MS: m/z 403 [M+H]$^+$.

Example 12

(R)-3-tert-butyl-4-(2,6-diisopropoxyphenyl)-2,3-dihydrobenzo[d][1,3]oxaphosphole (R)-3-tert-butyl-4-(2,6-diisopropoxyphenyl)-2,3-dihydrobenzo[d][1,3]oxaphosphole was prepared under a similar condition described in Example 4; 95% yield; $^1$HNMR (400 MHz, CD$_2$Cl$_2$): δ=7.25 (t, J=7.9 Hz, 1H), 7.20 (t, J=8.4 Hz, 1H), 6.81 (d, J=8.4 Hz, 1H), 6.79 (m, 1H), 6.55 (t, J=8.9 Hz, 2H), 4.71 (dd, J=12.5, 1.6 Hz, 1H), 4.30-4.55 (m, 3H), 1.27 (d, J=6.4 Hz, 3H), 1.25 (d, J=6.6 Hz, 3H), 1.15 (d, J=6.0 Hz, 3H), 1.10 (d, J=6.0 Hz, 3H), 0.73 (d, J=12.0 Hz); $^{31}$PNMR (162 MHz, CD$_2$Cl$_2$): δ=−6.0; $^{13}$CNMR (100 MHz, CD$_2$Cl$_2$): δ=163.9, 157.1, 156.5, 139.9 (d, J=17.8 Hz), 130.4, 129.2, 124.8 (d, J=4.4 Hz), 121.7, 109.2, 106.9, 105.1, 71.4, 70.8 (d, J=27.6 Hz), 69.8, 31.2 (d, J=19.0 Hz), 27.2 (d, J=14.7 Hz), 22.8 (d, J=4.5 Hz), 22.7, 22.5, 22.4; ESI-MS: m/z 387 [M+H]$^+$.

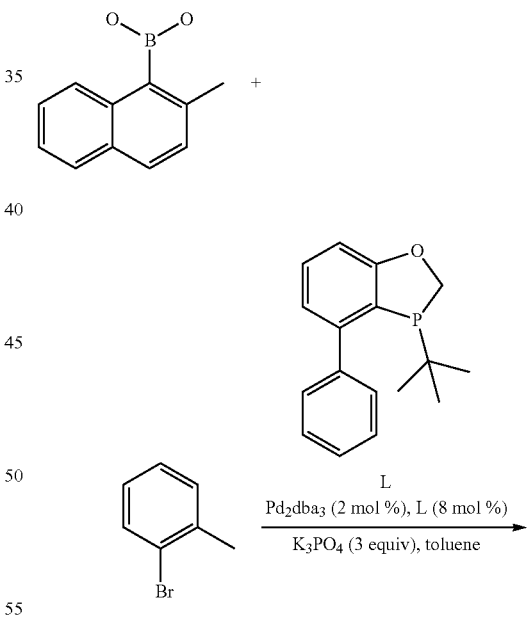

Experiment 13

2-methyl-1-o-tolylnaphthalene (A Typical Example of Suzuki-Miyaura Coupling Catalyzed by a Metal Complex of a Ligand According to the Present Invention as Described herein Above)

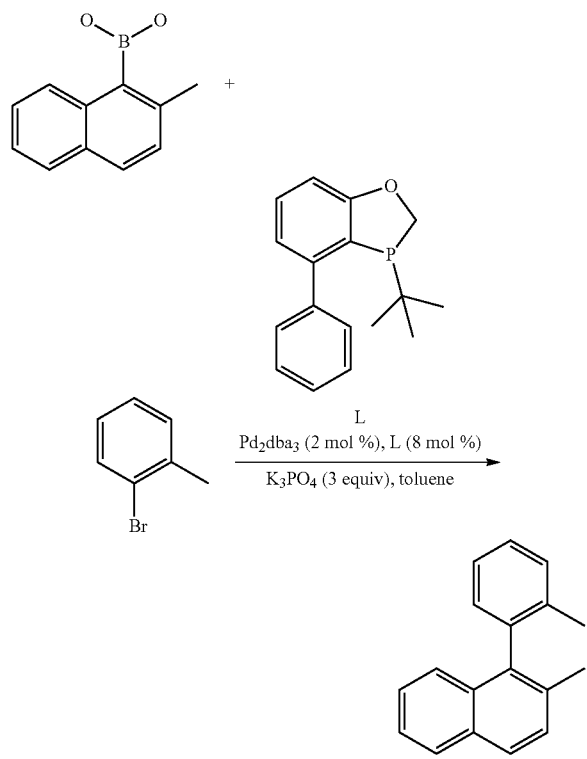

To a mixture of 2-methylnaphthalen-1-ylboronic acid (0.15 g, 0.75 mmol, 1.5 equiv) and 1-bromo-2-methylbenzene (86 mg, 0.5 mmol, 1.0 equiv), tris(dibenzylideneacetone)dipalladium (9.16 mg, 0.01 m mol, 2 mol %), 3-tert-butyl-4-phenyl-2,3-dihydrobenzo[d][1,3]oxaphosphole (11 mg, 0.04 mmol, 8 mol %), and potassium phosphate (0.318 g, 1.5 mmol, 3 equiv) was charged dagassed toluene (4 mL). The mixture was stirred at 70° C. under nitrogen for 24 h, then quenched with water (4 mL). The organic phase was separated, washed with brine, dried over sodium sulfate, concentrated, and purified by column chromatography to provide pure desired product as oil (95 mg, 0.41 mmol, 82%). ESI-MS: m/z 233 [M+H]$^+$

Experiment 14

2'-phenyl-2,4,6-trimethylbiphenyl

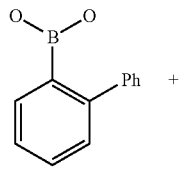

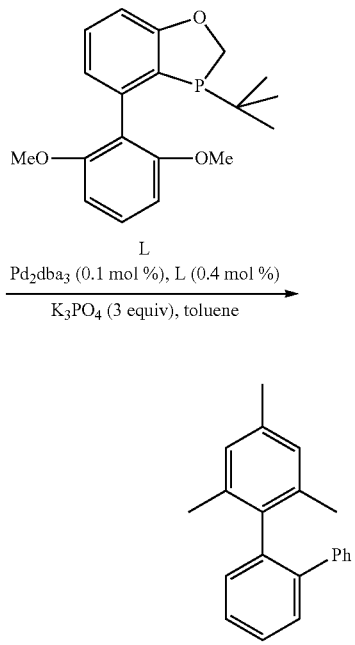

To a mixture of biphenyl-2-ylboronic acid (0.15 g, 0.75 mmol, 1.5 equiv) and 2-bromo-1,3,5-trimethylbenzene (100 mg, 0.5 mmol, 1.0 equiv), tris(dibenzylideneacetone)dipalladium (0.46 mg, 0.0005 m mol, 0.1 mol %), 3-tert-butyl-4-(2,6-dimethoxyphenyl)-2,3-dihydrobenzo[d][1,3]oxaphosphole (0.66 mg, 0.04 mmol, 0.4 mol %), and potassium phosphate (0.318 g, 1.5 mmol, 3 equiv) was charged dagassed toluene (4 mL). The mixture was stirred at 70° C. under nitrogen for 3 h, then quenched with water (4 mL). The organic phase was separated, washed with brine, dried over sodium sulfate, concentrated, and purified by column chromatography to provide pure desired product as oil (129 mg, 0.48 mmol, 95%). ESI-MS: m/z 273 [M+H]$^+$.

The invention claimed is:

1. A compound of the formula (Ia), (Ib), or a mixture thereof:

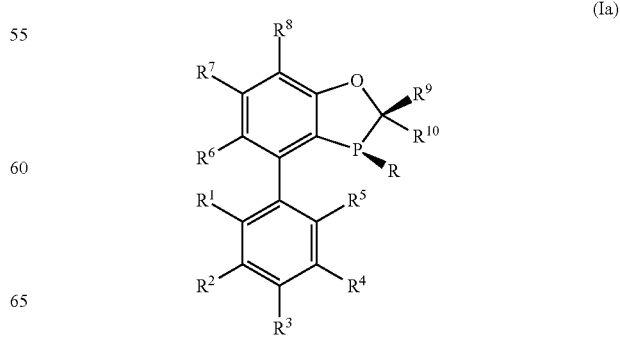

(Ia)

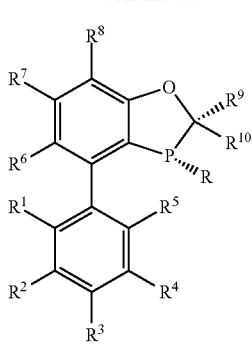

(Ib)

wherein:
R is (C$_1$-C$_6$)-alkyl, CF$_3$, (C$_3$-C$_{10}$)-carbocyclyl, (5- to 11-membered)heterocarbocyclyl, (C$_6$-C$_{10}$)aryl, (5 to 11-membered)heteroaryl, or ferrocenyl, wherein each such (C$_3$-C$_{10}$)carbocyclyl, (5- to 11-membered)heterocarbocyclyl, (C$_6$-C$_{10}$)aryl or (5 to 11-membered)heteroaryl group is optionally substituted with 1 to 3 substituents independently selected from the group consisting of —O(C$_1$-C$_6$)alkyl, (C$_1$-C$_6$)alkyl, and CF$_3$;

R$^1$, R$^2$, R$^3$, R$^4$, R$^5$ are each independently selected from the group consisting of H, halo, CF$_3$, —O(C$_1$-C$_6$)alkyl, (C$_1$-C$_6$)alkyl, (C$_3$-C$_{10}$)carbocyclyl, (5- to 11-membered)heterocarbocyclyl, (C$_6$-C$_{10}$)aryl, (5 to 11-membered)heteroaryl, —NR$^{11}$R$^{12}$, —Si(R$^{11}$)$_3$ and —SR$^{11}$, wherein each such (C$_3$-C$_{10}$)carbocyclyl, (5- to 11-membered)heterocarbocyclyl, (C$_6$-C$_{10}$)aryl or (5 to 11-membered)heteroaryl group is optionally substituted with 1 to 3 substituents independently selected from the group consisting of —O(C$_1$-C$_6$)alkyl, (C$_1$-C$_6$)alkyl and CF$_3$; or any two adjacent instances of R$^1$, R$^2$, R$^3$, R$^4$, R$^5$, taken together with the carbons to which they are bound, form a five- or six-membered substituted or unsubstituted aryl or heteroaryl ring; provided that at least one of R$^1$, R$^2$, R$^3$, R$^4$, R$^5$ are OR$^{11}$;

R$^6$, R$^7$, R$^8$ are each independently selected from the group consisting of H, CF$_3$, —O(C$_1$-C$_6$)alkyl, (C$_1$-C$_6$)alkyl, (C$_3$-C$_{10}$)carbocyclyl, (5- to 11-membered)heterocarbocyclyl, (C$_6$-C$_{10}$)aryl, (5 to 11-membered)heteroaryl and —NR$^{11}$R$^{12}$; wherein each such (C$_3$-C$_{10}$)carbocyclyl, (5- to 11-membered)heterocarbocyclyl, (C$_6$-C$_{10}$)aryl or (5 to 11-membered)heteroaryl group is optionally substituted with 1 to 3 substituents independently selected from the group consisting of —O(C$_1$-C$_6$)alkyl, (C$_1$-C$_6$)alkyl, and CF$_3$;

R$^9$, R$^{10}$ are each independently selected from the group consisting of H, (C$_1$-C$_6$)alkyl, (C$_3$-C$_6$)cycloalkyl, (3- to 6-membered)heterocycloalkyl, (C$_6$-C$_{10}$)aryl, (5- to 6-membered)heteroaryl, and —SiR$^5$$_3$; wherein each such (C$_3$-C$_6$)cycloalkyl, (3- to 6-membered)heterocycloalkyl, (C$_6$-C$_{10}$)aryl or (5- to 6-membered)heteroaryl group is optionally substituted with 1 to 3 substituents independently selected from the group consisting of —O(C$_1$-C$_6$)alkyl, (C$_1$-C$_6$)alkyl, and CF$_3$; and R$^{11}$ and R$^{12}$ are each independently selected from the group consisting of H, (C$_1$-C$_6$)alkyl, CF$_3$, (C$_3$-C$_{10}$)carbocyclyl, (5- to 11-membered)heterocarbocyclyl, (C$_6$-C$_{10}$)aryl, and (5 to 11-membered)heteroaryl, wherein each such (C$_3$-C$_{10}$)carbocyclyl, (5- to 11-membered)heterocarbocyclyl, (C$_6$-C$_{10}$)aryl or (5 to 11-membered)heteroaryl group is optionally independently substituted with 1 to 3 substituents independently selected from the group consisting of halo, —O(C$_1$-C$_6$)alkyl, (C$_1$-C$_6$)alkyl, and —CF$_3$.

2. A compound of formula (Ia), (Ib), or a mixture thereof, in accordance with claim 1, wherein R is —(C$_1$-C$_6$)alkyl selected from —CH$_3$, —CH$_2$CH$_3$, —CH(CH$_3$)$_2$, —C(CH$_3$)$_3$, —C(CH$_2$CH$_3$)$_3$, and —C(CH$_2$CH$_3$)(CH$_3$)$_2$.

3. A compound of formula (Ia), (Ib), or a mixture thereof, in accordance with claim 1, wherein R is —(C$_3$-C$_{10}$)carbocyclyl selected from cyclopentyl, cyclohexyl, and 1-adamantyl.

4. A compound of formula (Ia), (Ib), or a mixture thereof, in accordance with claim 1, wherein R is —(C$_6$-C$_{10}$)aryl selected from phenyl, ortho-tolyl, para-tolyl, 3,5-dimethylphenyl, 3,5-di-t-butylphenyl, 3,5-di-CF$_3$-phenyl, ortho-CF$_3$-phenyl, ortho-anisyl, and naphthyl.

5. A compound of formula (Ia), (Ib), or a mixture thereof, in accordance with claim 1, wherein R$^1$, R$^2$, R$^3$, R$^4$, R$^5$ are each independently H, —CH$_3$, —CH$_2$CH$_3$, —CH(CH$_3$)$_2$, —C(CH$_3$)$_3$, —OCH$_3$, —OCH$_2$CH$_3$, —OCH(CH$_3$)$_2$, N(CH$_3$)$_2$, N(CH$_2$CH$_3$)$_2$, or SiMe$_3$.

6. A compound of formula (Ia), (Ib), or a mixture thereof, in accordance with claim 1, wherein R$^6$, R$^7$, R$^8$ are H.

7. A compound of formula (Ia), (Ib), or a mixture thereof, in accordance with claim 1, wherein R$^9$ and R$^{10}$ are each independently H, —CH$_3$, —CH$_2$CH$_3$, —CH(CH$_3$)$_2$, —C(CH$_3$)$_3$, phenyl, ortho-tolyl, para-tolyl, 3,5-dimethylphenyl, 3,5-di-t-butylphenyl, 3,5-di-CF$_3$-phenyl, ortho-CF$_3$-phenyl, ortho-anisyl, 2,6-dimethoxyphenyl or naphthyl.

8. A phosphine ligand having the formula (IIa) or (IIb), or a mixture thereof,

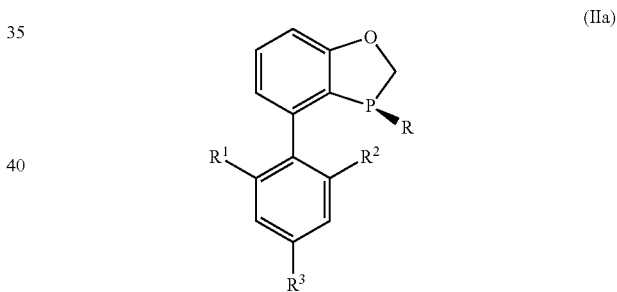

(IIa)

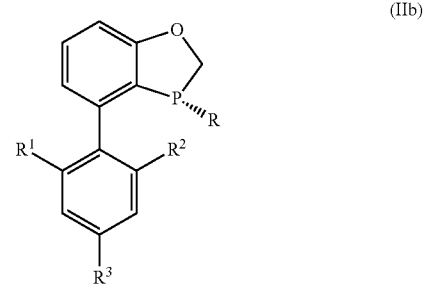

(IIb)

wherein:
R is —CH(CH$_3$)$_2$, —C(CH$_3$)$_3$ —C(CH$_2$CH$_3$)(CH$_3$)$_2$, cyclohexyl, 1-adamantyl, phenyl, ortho-tolyl, 3,5-xylyl, ortho-anisyl, or ferrocenyl; and R$^1$, R$^2$, and R$^3$ are independently H, —CH$_3$, —CH$_2$CH$_3$, —CH(CH$_3$)$_2$, —C(CH$_3$)$_3$, —OCH$_3$, —OCH$_2$CH$_3$, —OCH(CH$_3$)$_2$, OPh, N(CH$_3$)$_2$, N(CH$_2$CH$_3$)$_2$, SiMe$_3$, CF$_3$.

9. A phosphine ligand selected from the group consisting of:

(S) and (R)-3-tert-butyl-4-phenyl-2,3-dihydrobenzo[d][1,3]oxaphosphole, (S) and (R)-3-tert-butyl-4-(2,6-dimethoxyphenyl)-2,3-dihydrobenzo[d][1,3]oxaphosphole, (S) and (R)-2-(3-tert-butyl-2,3-dihydrobenzo[d][1,3]oxaphosphol-4-yl)-N1,N1,N3,N3-tetramethylbenzene-1,3-diamine, (S) and (R)-2-(3-tert-butyl-2,3-dihydrobenzo[d][1,3]oxaphosphol-4-yl)-N,N-dimethylaniline, (S) and (R)-3-tert-butyl-4-(2-methoxyphenyl)-2,3-dihydrobenzo[d][1,3]oxaphosphole, (S) and (R)-3-tert-butyl-4-(2,6-diisopropoxyphenyl)-2,3-dihydrobenzo[d][1,3]oxaphosphole, (S) and (R)-3-tert-butyl-4-(2,4,6-triisopropylphenyl)-2,3-dihydrobenzo[d][1,3]oxaphosphole, (S) and (R)-3-tert-butyl-4-o-tolyl-2,3-dihydrobenzo[d][1,3]oxaphosphole, (S) and (R)-3-tert-butyl-4-(2-phenoxyphenyl)-2,3-dihydrobenzo[d][1,3]oxaphosphole, (S) and (R)-3-cyclohexyl-4-phenyl-2,3-dihydrobenzo[d][1,3]oxaphosphole, (S) and (R)-3-cyclohexyl-4-(2,6-dimethoxyphenyl)-2,3-dihydrobenzo[d][1,3]oxaphosphole, (S) and (R)-2-(3-cyclohexyl-2,3-dihydrobenzo[d][1,3]oxaphosphol-4-yl)-N1,N1,N3,N3-tetramethylbenzene-1,3-diamine, (S) and (R)-2-(3-cyclohexyl-2,3-dihydrobenzo[d][1,3]oxaphosphol-4-yl)-N,N-dimethylaniline, (S) and (R)-3-cyclohexyl-4-(2-methoxyphenyl)-2,3-dihydrobenzo[d][1,3]oxaphosphole, (S) and (R)-3-cyclohexyl-4-(2,4,6-triisopropylphenyl)-2,3-dihydrobenzo[d][1,3]oxaphosphole, (S) and (R)-3-cyclohexyl-4-(2,6-diisopropoxyphenyl)-2,3-dihydrobenzo[d][1,3]oxaphosphole, (S) and (R)-3-cyclohexyl-4-o-tolyl-2,3-dihydrobenzo[d][1,3]oxaphosphole, and (S) and (R)-3-cyclohexyl-4-(2-phenoxyphenyl)-2,3-dihydrobenzo[d][1,3]oxaphosphole.

\* \* \* \* \*